(12) United States Patent
Umezawa et al.

(10) Patent No.: US 8,748,117 B2
(45) Date of Patent: Jun. 10, 2014

(54) PROBE FOR DETECTION AND QUANTIFICATION OF NITRIC OXIDE, AND METHOD FOR DETECTING AND QUANTIFYING NITRIC OXIDE USING THE SAME

(75) Inventors: Yoshio Umezawa, Tokyo (JP); Moritoshi Sato, Tokyo (JP)

(73) Assignee: Japan Science and Technology Agency, Saitama (JP)

( * ) Notice: Subject to any disclaimer, the term of this patent is extended or adjusted under 35 U.S.C. 154(b) by 0 days.

(21) Appl. No.: 13/103,317

(22) Filed: May 9, 2011

(65) Prior Publication Data

US 2011/0312014 A1  Dec. 22, 2011

Related U.S. Application Data

(62) Division of application No. 11/631,422, filed as application No. PCT/JP2005/012722 on Jul. 5, 2005, now abandoned.

(30) Foreign Application Priority Data

Jul. 5, 2004  (JP) ................................. 2004-198239

(51) Int. Cl.
  *G01N 33/53*  (2006.01)
(52) U.S. Cl.
  USPC .......................................................... 435/7.6
(58) Field of Classification Search
  None
  See application file for complete search history.

(56) References Cited

U.S. PATENT DOCUMENTS

2002/0137115 A1*  9/2002  Umezawa et al. .............. 435/15

FOREIGN PATENT DOCUMENTS

| JP | 2000-224986 | 8/2000 |
|---|---|---|
| JP | 2002/003069 | 1/2002 |

OTHER PUBLICATIONS

Joshua S. Krumenacker, Khalid A. Hanafy, Ferid Murad. Regulation of nitric oxide and soluble guanylyl cyclase. 2004 (available online Apr. 29, 2003). Brain Research Bulletin. 62:6. 505-515.*
Ralph L. Brinster, et al. Factors affecting the efficiency of introducing foreign DNA into mice by microinjecting eggs. 1985. Proceedings of the National Academy of Sciences. 82. 4438-4442.*
Akira Honda et al. Spatiotemporal dynamics of guanosine 3',5'-cyclic monophosphate revealed by a genetically encoded, fluorescent indicator. 2001. Proceedings of the National Academy of Sciences. 98:5 2437-2442.*
Miyawaki, A. et al. Fluorescent indicators for Ca2+ based on green fluorescent proteins and calmodulin. 1997. Nature. 388:882-887.*
International Search Report issued Sep. 27, 2005 in International (PCT) Application No. PCT/JP2005/012722.
Krumenacker et al., "Regulation of nitric oxide and soluble guanylyl cyclase," *Brain Research Bulletin* (2004), vol. 62, pp. 505-515.
Wagner et al., "Dimerization of Nitric Oxide-sensitive Guanylyl Cyclase Requires the $\alpha_1$ N Terminus," *The Journal of Biological Chemistry* (2005), vol. 280, No. 18, pp. 17687-17693.
Buechler et al., "Expression of soluble guanylate cyclase activity requires both enzyme subunits," *Biochemical and Biophysical Research Communications* (1991), vol. 174, No. 1, pp. 351-357.
Stengl et al., "Localization of cGMP immunoreactivity and of souble guanylyl cyclase in antennal sensilla of the hawkmoth *Manduca sexta*," *Cell Tissue Research* (2001), vol. 304, pp. 409-421.
Honda et al., "Spatiotemporal dynamics of guanosine 3',5'-cyclic monophosphate revealed by a genetically encoded, fluorescent indicator," *PNAS* (2001), vol. 98, No. 5, pp. 2437-2442.
Supplementary European Search Report issued Nov. 5, 2008 in European Application No. EP 05 75 7732.

* cited by examiner

*Primary Examiner* — David J Steadman
*Assistant Examiner* — Paul Holland
(74) *Attorney, Agent, or Firm* — Wenderoth, Lind & Ponack, L.L.P.

(57) ABSTRACT

Probe 1 for detection and quantification of nitric oxide, which comprises two subunits 21 and 22 of soluble guanylate cyclase 2 and cGMP-visualization probes 3 respectively connected with each subunit, wherein the cGMP-visualization probe generates signal upon recognizing guanosine 3',5'-cyclic monophospate.

1 Claim, 21 Drawing Sheets

A.

B.

A.

B.

NOA-1 :

FLAG: MDYKDDDDK
Ln: GGEQKLISEEDLLESR

A.

B.

A.

B.

A.

B.

A.

B.

A.

B.

A.

B.

A.

B.

A.

B.

C.

A.

CGY(T178A/T302A) Domain :

B.

NOA-2 :

FLAG: MDYKDDDDK
Ln: GGEQKLISEEDLLESR

PROBE FOR DETECTION AND QUANTIFICATION OF NITRIC OXIDE, AND METHOD FOR DETECTING AND QUANTIFYING NITRIC OXIDE USING THE SAME

This application is a Divisional of U.S. application Ser. No. 11/631,422, filed Feb. 26, 2007 now abandoned, which is a national stage application of International application No. PCT/JP2005/012722, filed Jul. 5, 2005, incorporated by reference in their entirety.

TECHNICAL FIELD

The invention of this application relates to a probe for detecting an intracellular nitric oxide, a method for detecting and quantifying nitric oxide using the same, and a method for screening a substance influencing the binding of nitric oxide to soluble guanylate cyclase, as well as a method for monitoring a change of nitric oxide concentration.

BACKGROUND ART

Since nitric oxide (NO) was reported to be an endothelium-derived relaxing factor in 1987, its various roles as a physiologically active substance have been found. NO is synthesized from L-arginine as a substrate by NO synthase (NOS), and controls a wide variety of biological responses not only in cardiovascular systems but also in immune systems and central nervous system, in which NO is involved in bio-defense response through macrophage or in acquisition of synaptic plasticity in memory and learning. It is also considered that NO relates to some diseases including arteriosclerosis, cerebral apoplexy and hypertension in cardiovascular systems, infectious diseases in immune systems, and dementia and Alzheimer's disease in central nervous system.

NO is an unstable and short-life molecule labile to oxidation with enzymes or reactive oxygen species in living body. So, it is difficult to detect NO at a physiological concentration, and therefore the dynamics of NO in living body is in an unknown area.

A method for detection of NO is a fluorescein derivative having a diamino group reacting with NO (diamino-fluoresceins; DAF) (Non-Patent document 1). Though DAF is not fluorescent in the absence of NO, it becomes to triazole to emit green fluorescence upon reacting with NO in the presence of dioxygen. Therefore, NO generation in a cell can be visualized with a fluorescence microscope. With a similar principle, a rhodamine derivative (DAR) emitting red fluorescence has also been reported (Non-Patent document 2).

There was a problem in the prior art, however, that these organic molecules easily accumulate in lipid membranes of cells and emit fluorescence signals there in an NO-independent manner thereby interfering with the detection of low concentration of NO in living cells. In addition, these organic molecules irreversibly react with NO, resulting in causing another problem that the complex dynamics of NO in living body such as a change of NO concentration cannot be followed.

The invention of this application was made to solve the above-mentioned problems in the prior art, and the purpose of the invention is to provide a new procedure for visualizing the change of NO concentration in the nM order precisely, conveniently and reversibly.

REFERENCE

Non-Patent document 1: Anal. Chem. 70; 2446-2453, 1998
Non-Patent document 2: Anal. Chem. 73: 1967-1973, 2001
Non-Patent document 3: Proc. Natl. Acad. Sci. USA 77: 7380-7384, 1980
Patent document 1: JP-A-2002-017359
Patent document 2: PCT/JP01/5631

DISCLOSURE OF INVENTION

The 1st invention of this application is a probe for detection and quantification of nitric oxide (hereinafter referred to as NO), which comprises two subunits of soluble guanylate cyclase (hereinafter referred to as sGC) and cGMP-visualization probes respectively connected with each subunit, wherein the cGMP-visualization probe generates signal upon recognizing guanosine 3',5'-cyclic monophospate (hereinafter referred to as sGMP).

The 2nd invention of this application is the above-identified probe, which is a dimmer of hybrid proteins, wherein the hybrid proteins are α- and β-subunits of sGC (hereinafter referred to as sGCα and sGCβ) respectively connecting with the cGMP-visualization probe.

The 3rd invention of this application is the above-identified probe, wherein the cGMP-visualization probe comprises cGMP-binding protein and two reporters connected with each end of the cGMP-binding protein so that the approach of the two reporters becomes detectable.

The 4th invention is the above-identified probe, wherein the cGMP-binding protein is cGMP-dependent protein kinase Iα.

The 5th invention is the above-identified probe, wherein the two reporters are yellow fluorescent protein and cyan fluorescent protein.

The 6th invention of this application is a method for detecting and quantifying NO, which comprises making the probe of any one of claims 1 to 5 to coexist with guanosine 5'-triphospate (hereinafter referred to as GTP), and measuring signal change.

The 7th invention is the above-identified method, wherein the probe coexists with GTP in a cell by introducing a polynucleotide expressing the probe into the cell.

The 8th invention is the above-identified method, wherein the probe coexists with GTP in a cell by introducing a pair of polynucleotides respectively expressing a hybrid protein into the cell, wherein each of the hybrid protein comprises sGCα or sGCβ connecting with the cGMP-visualization probe.

The 9th invention is the above-identified method, wherein the probe coexists with GTP in all cells of a non-human animal or its progeny established by introducing polynucleotide expressing the probe into a non-human totipotent cell and developing the cell to individual.

The 10th invention is the above-identified method, wherein the probe coexists with GTP in all cells of a non-human animal or its progeny established by introducing a pair of polynucleotides respectively expressing a hybrid protein into the cell, wherein each of the hybrid protein comprises sGCα or sGCβ connecting with the cGMP-visualization probe.

The 11th invention of this application is a method for screening a substance acting on binding of NO to sGC, which comprises making the above-identified probe coexist with GTP, a candidate substance and NO, and measuring signal change with and without the candidate substance.

The 12th invention is the above-identified screening method, wherein the probe coexists with GTP, a candidate substance and NO in a cell by introducing a polynucleotide expressing the probe and then the candidate substance into the cell.

The 13th invention is the above-identified screening method, wherein the probe coexists with GTP, a candidate substance and NO in a cell by introducing a pair of polynucleotides respectively expressing a hybrid protein into the cell, wherein each of the hybrid protein comprises sGCα or sGCβ connecting with the cGMP-visualization probe.

The 14th invention is the above-identified screening method, wherein the probe coexists with GTP, a candidate substance and NO in all cells of a non-human animal or its progeny by administering the candidate substance to the animal or its progeny, wherein the animal is established by introducing polynucleotide expressing the probe into a non-human totipotent cell and developing the cell to individual.

The 15th invention is the above-identified screening method, wherein the probe coexists with GTP, a candidate substance and NO in all cells of a non-human animal or its progeny by administering the candidate substance to the animal or its progeny, wherein the animal is established by introducing a pair of polynucleotides respectively expressing a hybrid protein into a non-human totipotent cell and developing the cell to individual, and wherein each of the hybrid protein comprises sGCα or sGCβ connecting with the cGMP-visualization probe.

The 16th invention is a method for monitoring an intracellular change of NO concentration with a stimulation, which comprises introducing a polynucleotide expressing the above-identified probe into a cell, stimulating the cell, and measuring signals before and after the stimulation.

The 17th invention is a method for monitoring an intracellular change of NO concentration with a stimulation, which comprises introducing a pair of polynucleotides respectively expressing a hybrid protein, stimulating the cell, and measuring signals before and after the stimulation, wherein each of the hybrid protein comprises sGCα or sGCβ connecting with the cGMP-visualization probe.

The 18th invention is a method for monitoring an intracellular change of NO concentration with a stimulation, which comprises stimulating a non-human animal or its progeny, and measuring signals before and after the stimulation, wherein the animal is established by introducing polynucleotide expressing the probe of any one of claims 1 to 5 into a non-human totipotent cell and developing the cell to individual.

The 19th invention is a method for monitoring an intracellular change of NO concentration with a stimulation, which comprises stimulating a non-human animal or its progeny, and measuring signals before and after the stimulation, wherein the animal is established by introducing a pair of polynucleotides respectively expressing a hybrid protein into a non-human totipotent cell and developing the cell to individual, and wherein each of the hybrid protein comprises sGCα or sGCβ connecting with the cGMP-visualization probe.

In the probe of the 1st invention, a cGMP-visualization probe is linked with each of two subunits of sGC. The sGC increases its enzymatic activity up to 200 times or more upon binding of NO to the heme iron of sGC, which then generates a large amount of second messenger cGMP from GTP. The cGMP-visualization probe site recognizes the cGMP and emits a signal. Thus, measurement of the signal change allows highly precise detection of NO.

The probe of the 2nd invention may be prepared by dimerizing two hybrid proteins which comprise sGCα and sGCβ respectively connecting with the cGMP-visualization probe, and the two subunits reconstruct the sGC by dimerizing of the two hybrid proteins.

In the probe of the 3rd invention, the cGMP-visualization probe comprises cGMP-binding protein and two reporters connected to each end of the cGMP-binding protein so that the approach of the two reporters becomes detectable. That is, the sGC in the probe increases its enzymatic activity upon coordinate bonding of NO with the heme iron of sGC thereby generating cGMP. The cGMP then binds to the cGMP-binding protein to change the conformational change to make the two reporters at both ends of the cGMP-visualization probe become in close proximity each other. Thus, a signal is emitted and NO can be precisely detected.

As an embodiment of the cGMP-visualization probe, in the 4th invention, the cGMP-binding protein is cGMP-dependent protein kinase Iα (hereinafter, sometimes described as PKG Iα), and in the 5th invention, the two reporters are cyan fluorescent protein and yellow fluorescent protein, respectively.

In the method for detecting and quantifying NO of the 6th invention, the signal change of the probe may be measured in the presence of the probe and GTP. That is, coordinate bonding of NO with the heme iron of the sGC site of NO probe increases the enzymatic activity of sGC, and generates a large amount of cGMP using the coexisting GTP, a substrate. Thus, the cGMP-visualization probe site of the probe recognizes the cGMP to emit a signal. The calibration curve between NO concentrations and the signal changes allows the quantification of NO.

In the 7th invention, a polynucleotide expressing the probe is introduced into a cell thereby the probe coexists with GTP in the cell. In the 8th invention, the probe coexists with GTP in a cell by introducing a pair of polynucleotides respectively expressing a hybrid protein into the cell, wherein each of the hybrid protein comprises sGCα or sGCβ connecting with the cGMP-visualization probe. The pair of hybrid proteins forms a dimer to constitute sGC in the cell.

In the 9th invention, a non-human animal or its progeny is established by introducing polynucleotide expressing the probe into a non-human totipotent cell and developing the cell to individual, by which the probe coexists with GTP in all cells of the non-human animal or its progeny. In the 10th invention, a non-human animal or its progeny is established by introducing a pair of polynucleotides respectively expressing a hybrid protein into the cell, wherein each of the hybrid protein comprises sGCα or sGCβ connecting with the cGMP-visualization probe. The pair of hybrid proteins forms a dimer to constitute sGC. Consequently, the probe and GTP coexist in all cells of the animal or its progeny.

In the screening method of the 11th invention, the above-identified probe coexists with GTP, a candidate substance and NO, and then signal changes are measured with and without the candidate substance, thereby a substance acting on binding of NO to sGC can be screened.

In the screening method of the 12th invention, coexistence of the probe, GTP and a candidate substance in a cell is achieved by introducing a polynucleotide expressing the probe and subsequently the candidate substance into the cell.

In the screening method of the 13th invention, the probe coexists with GTP and a candidate substance in a cell by introducing a pair of polynucleotides respectively expressing a hybrid protein into the cell, wherein each of the hybrid protein comprises sGCα or sGCβ connecting with the cGMP-visualization probe. The pair of hybrid proteins forms a dimer to constitute sGC in the cell, thereby it can coexist with GTP, the candidate and NO in the cell.

In the screening method of the 14th invention, the candidate substance is administered to a non-human animal or its progeny established by introducing polynucleotide expressing the probe into a non-human totipotent cell and developing the cell to individual, thereby the probe can coexists with GTP, a candidate substance and NO in all cells of the animal.

In the screening method of the 15th invention, the candidate substance is administered to a non-human animal or its progeny established by introducing a pair of polynucleotides respectively expressing a hybrid protein into a non-human totipotent cell and developing the cell to individual. Each of the hybrid protein comprises sGCα or sGCβ connecting with the cGMP-visualization probe, and the pair of hybrid proteins forms a dimer to constitute sGC in all cells of the animal, thereby it can coexist with GTP, the candidate and NO in all cells of the animal.

In the 16th invention, a cell is introduced with a polynucleotide expressing the probe and signal changes from the cell are measured before and after stimulation, thereby intracellular changes of NO concentration with the stimulation can be monitored.

In the 17th invention, a cell is introduced with a pair of polynucleotides respectively expressing a hybrid protein into the cell, wherein each of the hybrid protein comprises sGCα or sGCβ connecting with the cGMP-visualization probe. Then, signal changes from the cell are measured before and after stimulation and intracellular change of NO concentration with the stimulation can be monitored.

In the 18th invention, intracellular changes of NO concentration can be monitored by stimulating a non-human animal or its progeny established by introducing polynucleotide expressing the probe into a non-human totipotent cell and developing the cell to individual, and measuring signal changes from the animal before and after stimulation.

In the 19th invention, the stimulation is provided to a non-human animal or its progeny established by introducing a pair of polynucleotides respectively expressing the hybrid protein comprising sGCα or sGCβ connecting with the cGMP-visualization probe into a non-human totipotent cell and developing the cell to individual. Intracellular change of NO concentration can be monitored by stimulating the animal and measuring signal changes before and after the stimulation.

The symbols used in Figures are as follows.
1: probe for detection and quantification of NO
2: soluble guanylate cyclase (sGC)
  21: α subunit
  22: β subunit
  23: heme iron
3: cGMP-visualization probe
  31: cGMP-binding protein
  32a: reporter
  32b: reporter

BEST MODE FOR CARRYING OUT THE INVENTION

Figure 1:
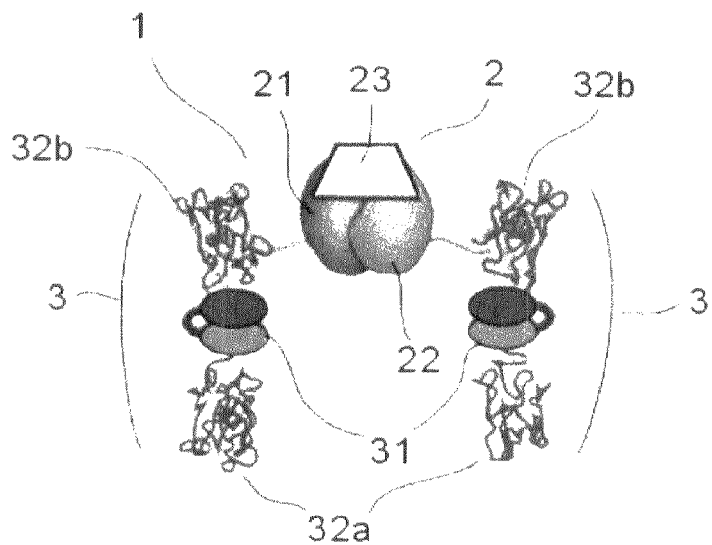
FIG. 1A is a schematic representation showing the constitution of the probe of the present invention.
FIG. 1B is the principle of signal detection by the probe of the present invention.
Figure 1:
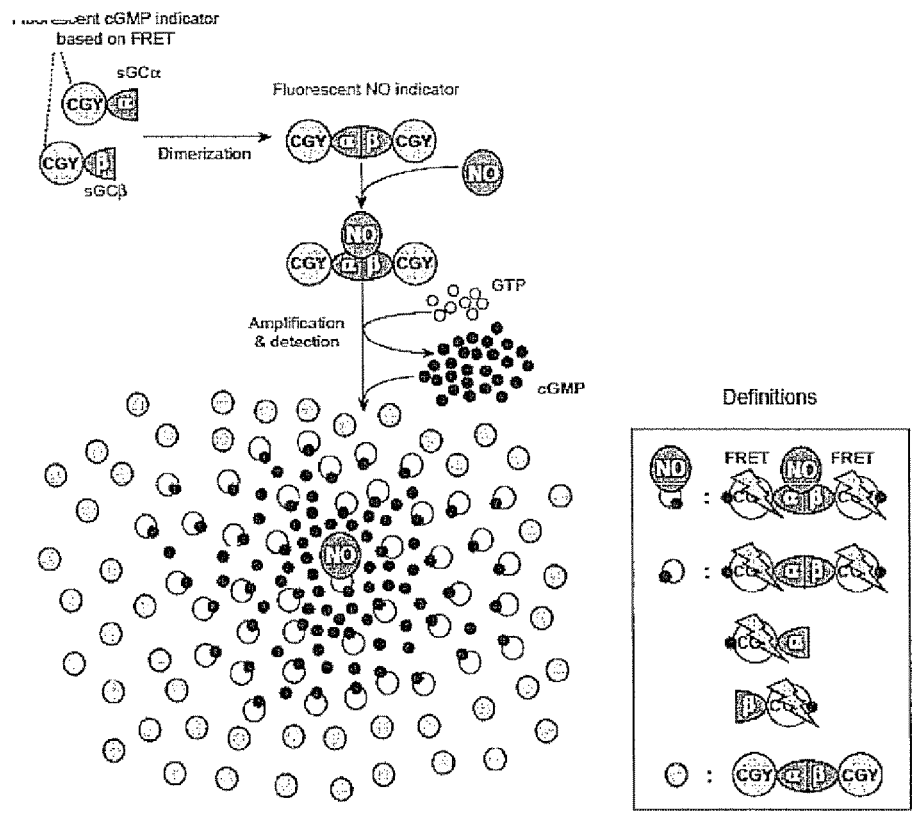

Probe 1 for detection and quantification of nitric oxide of the present invention is characterized in, as shown in FIG. 1A, two subunits α 21 and β 22 of sGC 2 and cGMP-visualization probe 3 connected to each of the subunit.

Probe 1 works on the basis of the following principle; after NO binding to heme iron 23 of sGC 2 increases the enzyme activity of sGC 2, resulting in generation of a large amount of cGMP; cGMP-visualized probe 3 in probe 1 recognizes cGMP and emits a signal. FIG. 1B is a schematic representation of the principle.

Therefore, in other words, probe 1 amplifies the changes in NO concentration at the sGC 2, and detects the signal changes emitted from the cGMP-visualized probe 3 due to the changes of cGMP concentration.

Since NO reversibly binds to heme iron 23, NO forms a coordination bond with heme iron 23, and the bound NO is released from heme iron 23 which results in loss of the enzyme activity at sGC 2. As a result, cGMP generation is stopped. In addition, under the presence of phosphodiesterase (PDE), only degradation of cGMP by PDE proceeds to decrease the cGMP concentration, which appears as a signal change of cGMP-visualized probe 3.

Therefore, probe 1 can reversibly react with NO of its differing concentrations.

In probe 1, while there is no particular limitation for cGMP-visualization probe 3 as far as it recognizes cGMP and emits a signal, the probe reported by the present inventors (Patent documents 1 and 2) is preferable. The cGMP-visualization probe by the present inventors comprises two reporters 32a and 32b connected to both ends of cGMP-binding protein 31 so that their mutual approach is detectable. In such cGMP-visualization probe 3, two reporters 32a and 32b changes their conformation upon binding of cGMP to cGMP-binding protein 31, which appears as an optical change. NO can be detected and quantified by measuring this optical change.

In cGMP-visualization probe 3, cGMP-binding protein 31 is exemplified by cGMP-depending protein kinase Iα (PKG Iα). PKG Iα of mammals consists of the two same monomers having four functional domains, in which the dimmer domain at the N-terminal consists of leucine/isoleucine zipper motif. At the absence of cGMP, while PKG Iα is kinase inactive and takes a closed conformation in which the catalytic center is occupied by the autoinhibition domain, the autoinhibition domain is removed from the active center, and PKG Iα has an open conformation upon cGMP binding thereto. In such a case, conformational changes of reporters 32a and 32b occurs to generate a visually detectable optical change.

Of course, cGMP-binding protein 31 is not limited to PKG Iα, and every kind of peptide chain including synthetic and natural ones may be used.

In cGMP-visualization probe 3, various chromophores may be used for two reporters 32a and 32b of which approach is detectable. In such a case, the chromophores are required to precisely generate a wavelength change with responding to the conformational change upon binding of cGMP to the cGMP-binding protein. Among various fluorescent chromophores in the field of biochemistry, some chromophores rapidly respond to a conformational change and alter the fluorescence intensity ratio based on fluorescence resonance energy transfer (hereinafter referred to as FRET). Accordingly, two fluorescent chromophores having different fluorescence wavelength are used for two reporters 32a and 32b, specifically including cyan fluorescent protein (CFP), a blue-shift variant of green fluorescent protein (GFP), and yellow fluorescent protein (YFP), a red-shift variant of GFP. Thus, the generation of cGMP can be detected as a change of emission ratio according to conventional and various methods used in chemical and biochemical analysis. Of course, in addition to a combination of CFP and YFP, various fluorescent proteins, split Renilla luciferase, firefly luciferase, β-galactosidase, β-lactamase, and the like may be applied as two reporters 32a and 32b.

In probe 1, sGC 2 is available from various organisms in nature.

In order to detect NO using probe 1, the signal changes may be measured in the coexistence of probe 1, GTP and NO. For example, probe 1 may be added to an elute of cell containing GTP thereby probe 1 coexists with GTP and NO. NO can be detected and quantify in vitro.

Alternatively, a polynucleotide expressing probe 1 may be introduced into cells so that probe 1 and GTP coexist in the cells. In this case, a plasmid vector for animal cells may preferably be used as an expression vector. Such a plasmid vector may be introduced into cells by means of conventional methods such as electroporation, calcium phosphate method, liposome method, DEAE dextran method, and the like. With introduction of such expression vector, probe 1 coexist with GTP in a cell. In general, GTP exists in live cells in a sufficient amount, and it is not necessary to add an additional amount. Of course, it may be added if required.

Further, probe 1 of the present invention may be a dimer of two hybrid proteins each comprising cGMP-visualization probe 3 connected to sGCα 21 or sGCβ 22.

In this case, probe 1 coexist with GTP and NO by introducing into cells a pair of polynucleotides respectively expressing a hybrid protein comprising sGCα 21 or sGCβ 22 connecting with the cGMP-visualization probe 3. sGCα 21 or sGCβ 22 are dimerized in cells to form sGC 4.

Thus, an intracellular endogenous or exogenous NO can be detected or quantified by making probe 1 coexist with GTP.

In addition, using cells having probe 1 and GTP, it may be possible to screen an inhibitor or antagonist for the binding of sGC with NO, or to monitor an influence of stimulation on the intracellular NO concentration change.

For example, it is possible to determine whether or not a candidate substance can inhibit the binding of NO to sGC 2 by measuring signal changes with and without the candidate substance. This case allows in vivo screening.

In addition, an influence of stimulation on the intracellular NO concentration can be monitored by measuring signal changes before and after the stimulation. For example, in the case where two reporters 32a, 32b of cGMP-visualization probe 3 are CFP and YFP, enhancement of the NO concentration decreases the emission ratio of CFP to YFP(CFP/YFP) with stimulation. Time course change of NO concentrations can be monitored by continuous measurement with the stimulation. The stimulation may be biochemical one such as hormone or endocrine disrupters, or physical one such as electricity, radiation or heat.

In the present invention, probe 1 coexists with GTP in all of the cells of a transgenic non-human animal. The transgenic non-human animal is established by introducing a polynucleotide expressing probe 1 into a non-human totipotent cell and developing the cell to individual according to a known method (e.g., Non-Patent document 3).

The transgenic non-human animal contains probe 1 and GTP in all of the somatic cells, and NO in living body can be detect or quantified by measuring signal changes with a stereoscopic fluorescence microscope or multiphoton laser scanning microscope. In addition, for example, an effect of a test substance such as a drug or a stimulation effect on the NO concentrations in cells, tissues or organs may be measured in living body. Influence of NO on vitality may be also examined. The transgenic non-human animal may be established by using a disease-model animal such as a gene defect animal. Using such animal, comparison of NO generations between the animal and a normal one can provide with a basic biological knowledge as to a physiological effect of NO.

Hereinafter, Examples will be shown along with Drawings to explain in more detail embodiments for carrying out the invention, while the invention is not limited by the following examples, and needless to say, various modifications are allowed in details.

Figure 2:
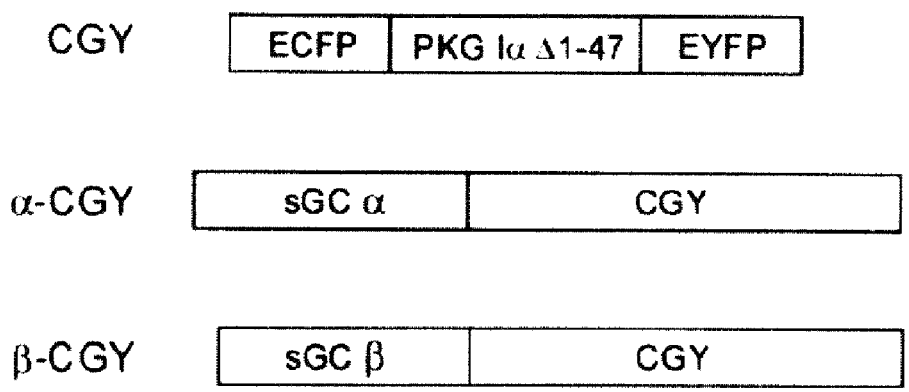
FIG. 2 shows cDNA constructs used in Examples. A, constructs for CGY, α-CGY and β-CGY; B, constructs for "sGCα-CGY" in which CGY is connected with α-CGY, and "sGCβ-CGY" in which CGY is connected with β-CGY.
Figure 2:
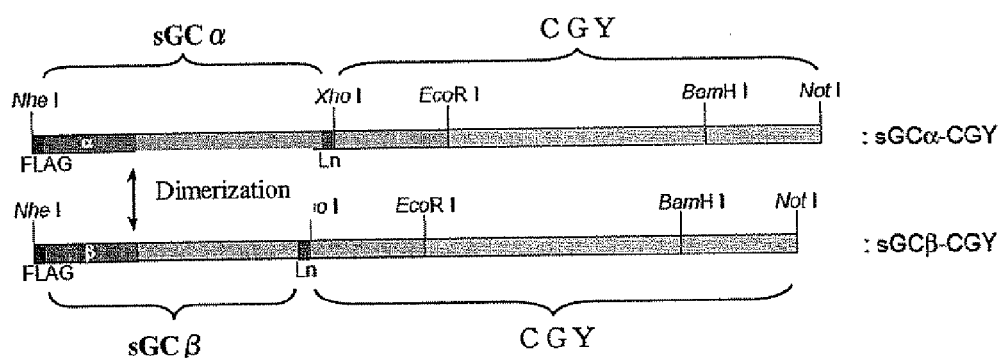

Example 1 cDNAs respectively expressing the hybrid proteins were constructed. The hybrid proteins respectively comprise cGMP-visualization probe (hereinafter described as CGY) connected with C-terminus of sGCα or sGCβ through the linker of SEC ID NO.1 (GGEQKLISEEDLLESR). The CYG was prepared according to the method in Patent documents 1 and 2. The heterodimmer of the hybrid proteins was named as "NOA-1" (fluorescent indicator for NO with a signal amplifier) (FIGS. 2A and B). At N-terminus of NOA-1, FLAG tag of SEC ID NO.2 (MDYKDDDDK) may be attached.

Two cDNAs were introduced into CHO K1 cells having little amount of endogenous sGC thereby coexpressing both sGCα-CGY and sGCβ-CGY in the cells. When these cells were stimulated with 5 nM of 3-(2-hydroxy-1-methylethyl-2-nitrosohydrazino)-N-methyl-1-propanamine (NOC-7), the CFP/YFP emission ratio immediately decreased but gradually recovered up to the initial level (FIG. 3-a).

Figure 3:
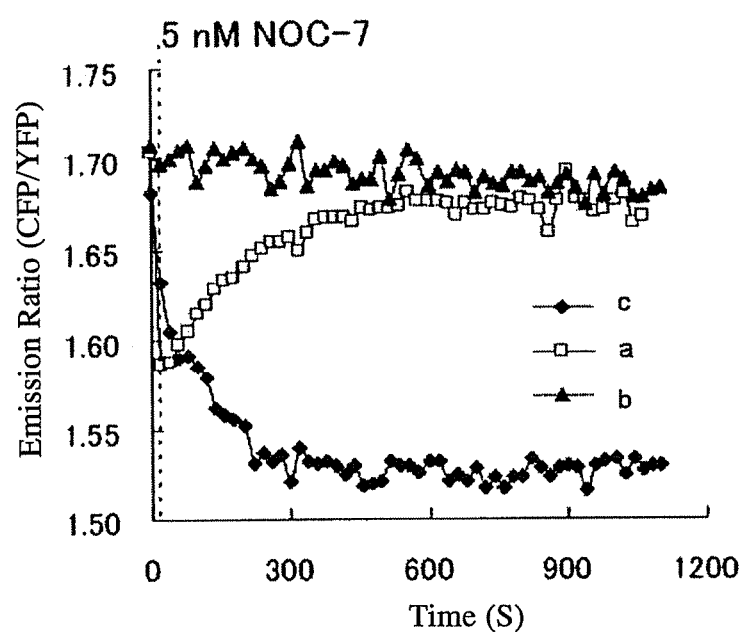
FIG. 3 shows time courses in CFP/YFP emission ratio in the cells expressing the probe of the present invention. The cells were stimulated with NOC-7 (5 nM). a: intact cell; b: cell pretreated with 100 μM of NS2028; c: cell pretreated with 200 μM of Zaprinast

The transient change in the emission ratio by 5 nM NOC-7, however, was completely blocked by pretreating the cells with NS 2028, an sGC inhibitor (FIG. 3-b).

The latter recovery of the decreased emission ratio disappeared when the cells were pretreated with an inhibitor of phosphodiesterases (PDE) that hydrolyses cGMP, zaprinast (FIG. 3-c).

These results indicate that sGC increases its enzymatic activity by NO generation with stimulation of 5 nM NOC-7 and generates cGMP in living cells, thereby CFP/YFP reaches the minimum level. The results also indicate that CFP/YFP recovered to the initial level due to the decrease of NO concentration and hydrolysis of cGMP by endogenous PDE in living cells.

Example 2

Figure 4:
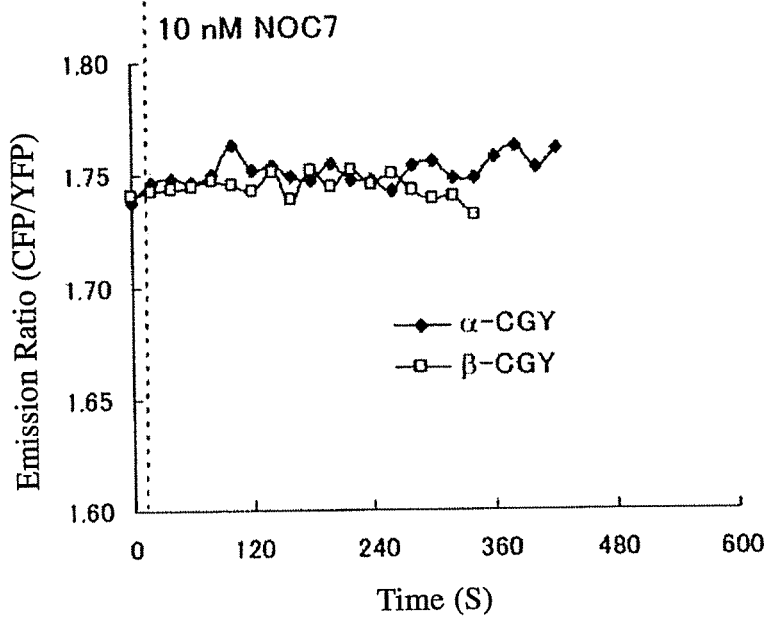
FIG. 4A shows time courses in CFP/YFP emission ratio in CHO-K1 cells respectively expressing α-CGY and β-CGY. The cells were stimulated with 10 nM NOC-7.
FIG. 4B shows time courses in CFP/YFP emission ratio in the cells, which were stimulated with 50 nM NOC-7 and after about 400 seconds, 8-Br-cGMP was added.
Figure 4:
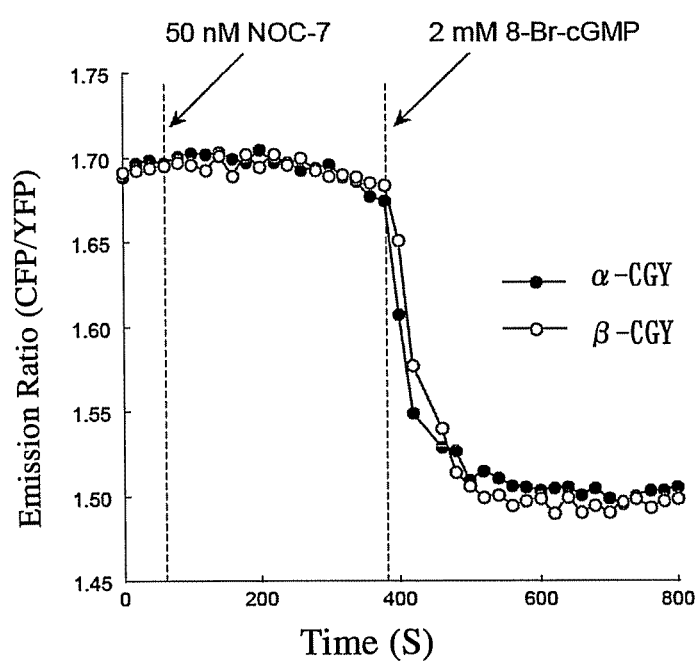

(1) When the CHO-K1 cells expressed with sGCα-CGY or sGCβ-CGY were respectively stimulated with 10 nM NOC-7, no significant change was observed in an emission ratio of CFP to YFP (FIG. 4).

Heme is known to bind to β-subunit, but from the results of FIG. 4, it was confirmed that the β-subunit alone has no enzymatic activity, and the reconstruction of sGC by dimerization of sGCα-CGY and sGCβ-CGY in the cell increases NO-dependent enzymatic activity.

(2) When the CHO-K1 cells expressing sGCα-CGY or sGCβ-CGY were stimulated with 50 nM NOC-7, no significant change was observed in an emission ratio of CFP to YFP (FIG. 4B). This flat fluorescence time course shows no change in the FRET efficiency in the CGY domain. However, subsequent addition of a membrane-permeable analogue of cGMP, 2 mM 8-Br-cGMP, immediately induced FRET in the CGY domain, according to a quick decrease in the CFP/YFP emission ratio (FIG. 4B).

This result indicates that sGCα-CGY alone and sGCβ-CGY alone do not have the catalytic cyclase activity to generate cGMP as expected, although the CGY domain works well as a cGMP indicator even when it is connected with sGCα or sGCβs.

Example 3

Figure 5:
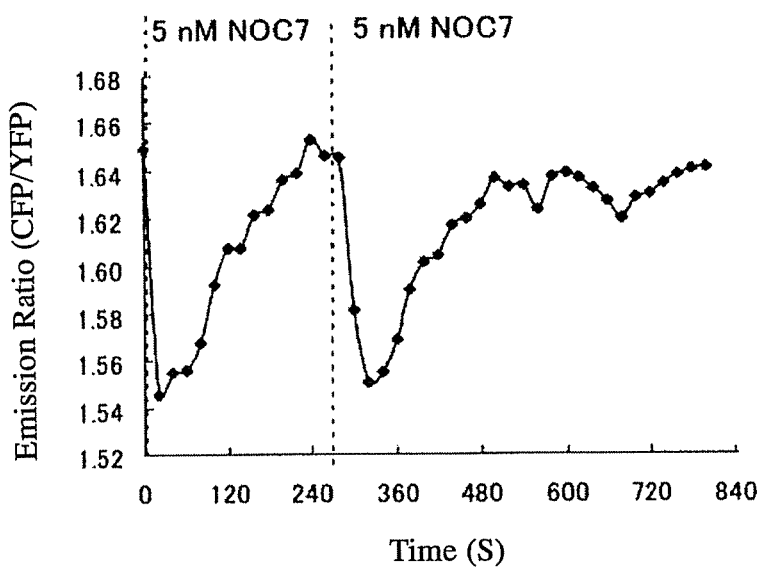
FIG. 5 shows time courses in CFP/YFP emission ratio in the cells expressing the probe of the present invention. The cells were repeatedly stimulated with NOC-7 (5 nM).

In the same manner as in Example 1, both sGCα-CGY and sGCβ-CGY were coexpressed in CHO-K1 cells. When these cells were stimulated with 5 nM NOC-7, the CFP/YFP emission ratio showed a transient response. After the emission ratio was recovered to the initial value, the cells showed the same transient response upon stimulation with 5 nM NOC-7 (FIG. 5).

This result indicates that the probe of this invention makes it possible to reversibly measure the cGMP changes correlating to NO changes.

Example 4

Figure 6:
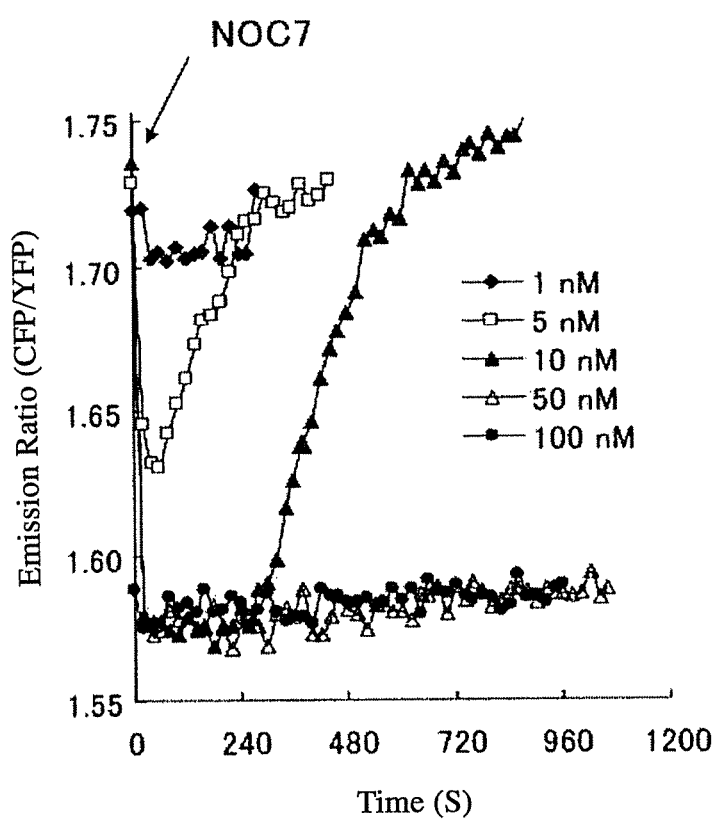
FIG. 6 shows time courses in CFP/YFP emission ratio in the cells expressing the probe of the present invention. The cells were stimulated with various concentrations of NOC-7.

In the same manner as in Example 1, the CHO-K1 cells coexpressed with both sGCα and sGCβ were stimulated with various amount of NOC-7 to measure the changes of CFP/YFP emission ratio dependent to NO concentrations (FIG. 6).

Upon stimulation with 1 nM or 5 nM NOC-7, a dose-dependent transient response was observed. With 10 nM NOC-7, the response reaches a plateau and then slowly recovered to the initial level with decrease of NO concentration. On the other hand, when the cells were stimulated with 50 nM or 100 nM NOC-7, the CFP/YFP emission ratio did not show no recovery to the initial level even after 20 minutes.

This result suggests that the NOC-7 stimulations of 50 nM or 100 nM generates a large amount of cGMP in the cells, and which is sufficient for saturation of CGY even after decrease of NO or hydrolysis cGMP by PDE.

From the above results, it was indicated the probe of this invention is highly sensitive to nanomolar concentrations of NO.

Example 5

Figure 7:
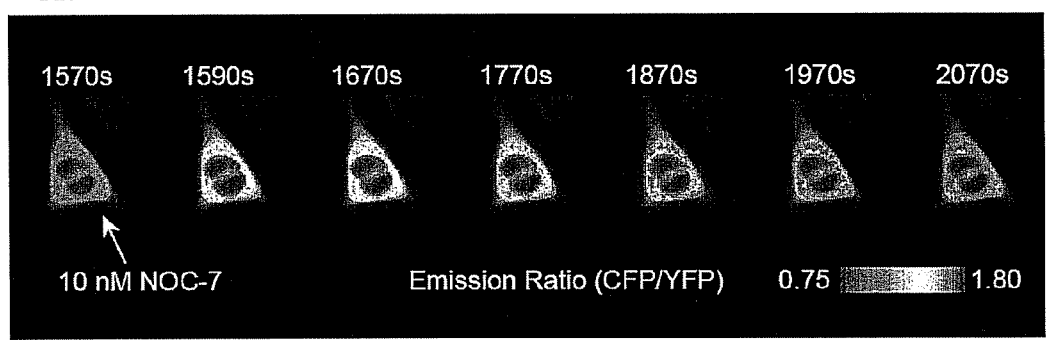
FIG. 7A shows pseudocolor images of the CFP/YFP emission ratio of NOA-1 upon stimulation with NOC-7.
FIG. 7B shows a reversible response of NOA-1 for various concentrations of NOC-7. CHO-K1 cells expressing NOA-1 were stimulated with various concentrations of NOC-7 and the CFP/YFP emission ratio was measured.
Figure 7:
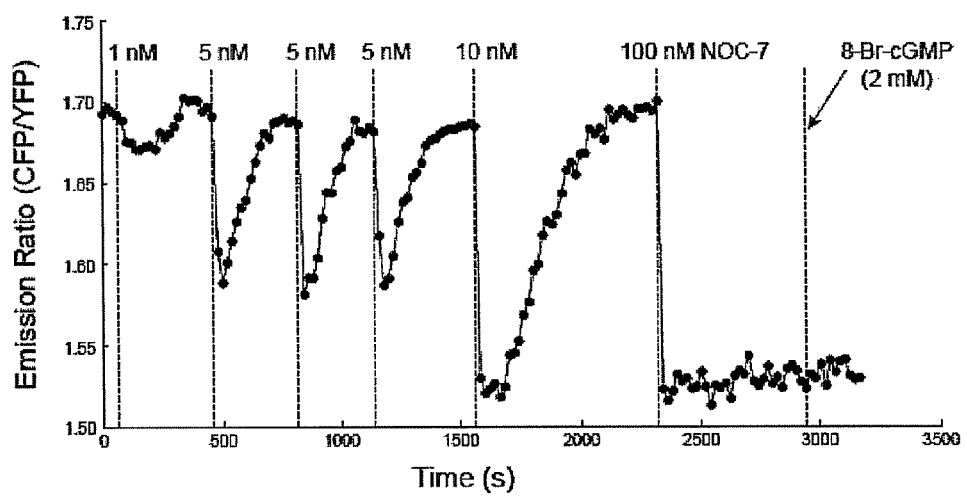

In the same manner as in Example 1, the CHO-K1 cells expressing NOA-1 were stimulated with various amount of NOC-7 to measure the changes of CFP/YFP emission ratio by NO and 8-Br-cGMP stimulations (FIGS. 7A and 7B).

When the cell expressing NOA-1 was stimulated with 1 nM or 5 nM NOC-7, NO-dependent transient change in the CFP/YFP emission ratio was observed. Also, upon addition of 10 nM NOC-7, a quick decrease was observed in the CFP/YFP emission ratio. The emission ratio then reached a plateau emission ratio, which was recovered up to the basal level. The CFP/YFP emission ratio reached the plateau as well immediately after the addition of 100 nM NOC-7; however, it did not subsequently show significant recovery for at least 10 min. The plateau responses obtained by 100 nM NOC-7 did not further decrease by the addition of 2 mM 8-Br-cGMP (FIG. 7B).

This result suggests again that the NOC-7 stimulations of 100 nM generates a large amount of cGMP in the cells, and which is sufficient for saturation of CGY even after decrease of NO or hydrolysis cGMP by PDE.

Example 6

Figure 8:
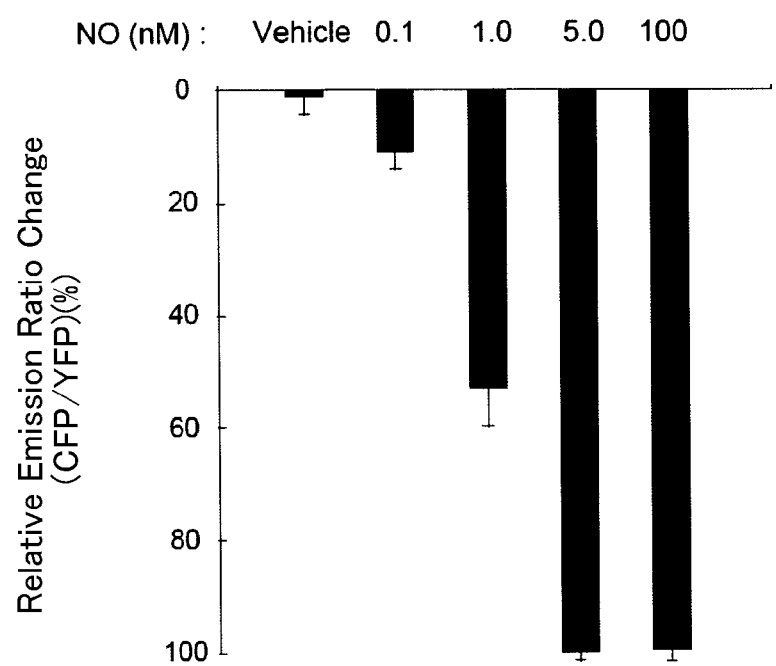
FIG. 8 shows dose-response of NOA-1 for the nanomolar range of NO.

The NO-dependent FRET response of NOA-1 was confirmed by using NO solutions prepared by bubbling NO gas. FIG. 8 shows the averaged peak response of NOA-1 at each concentration of NO in CHO-K1 cells. The NOA-1 was thus confirmed to detect the nanomolar range of NO. Importantly, NOA-1 senses not only an increase in the NO concentration but also its removal by oxidation and/or volatilization. This NO-dependent reversible response of NOA-1 is caused by the reversible binding of NO to the heme group in NOA-1 and endogenous phosphodiesterases that immediately hydrolyze the generated cGMP molecules after the removal of NO.

Example 7

As to the selectivity of NOA-1, the FRET response of NOA-1 for carbon monoxide (CO) was examined.

Figure 9:
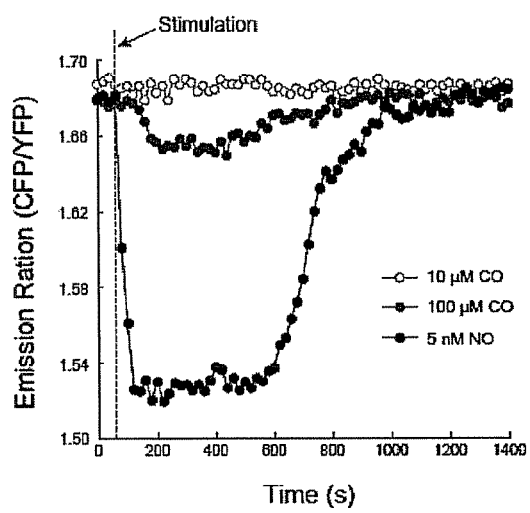
FIG. 9 shows selectivity of NOA-1. A, time courses of NOA-1 response with various concentration of carbon oxide (CO); B, reversible response of NOA-1.
Figure 9:
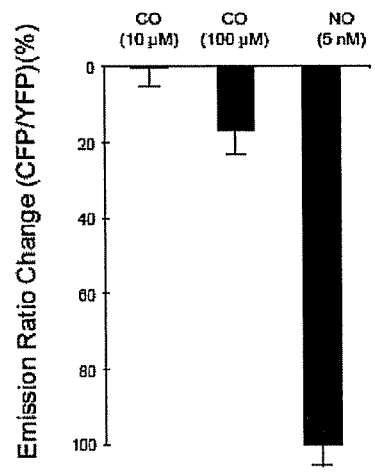

When CHO-K1 cells expressed with NOA-1 were stimulated with CO up to 10 µM, no significant change in the CFP/YFP emission ratio was observed (FIG. 9A). At 100 µM CO, a transient but much smaller response of NOA-1 was observed than that for 5 nM NO (FIG. 9B). CO is a sGC activator but has a lower affinity with sGC than NO. In addition, the CO-bound sGC is known to have much lower cyclase activity than NO-bound sGC because of each different coordination to the heme iron. Physiologically generated CO thus appears not to affect the response of NOA-1.

Example 8

Figure 10:
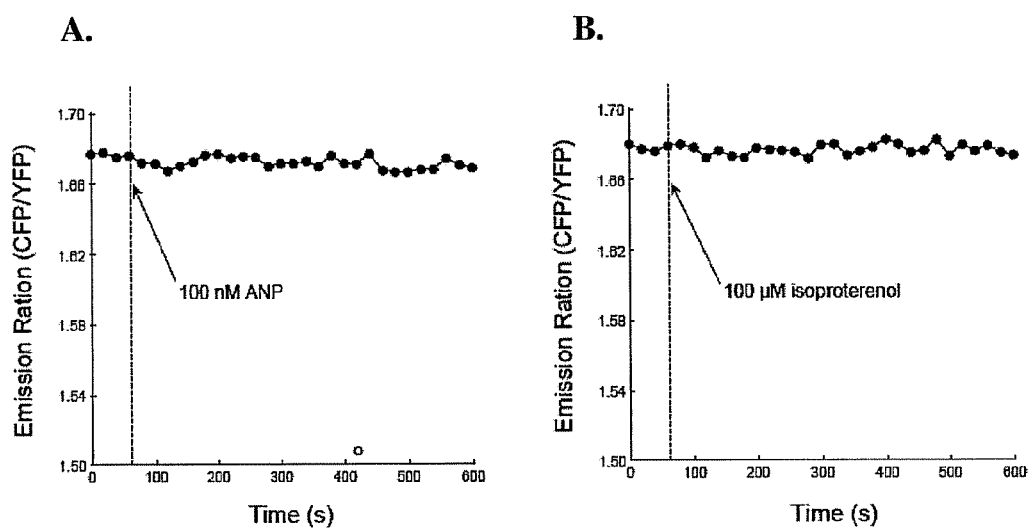
FIG. 10 shows time courses of NOA-1 response for ANP stimulation (A) and for isoproterenol stimulation (B) in CHO-K 1 cells.

Effect of natriuretic peptide stimulation or cAMP generation on the FRET response of NOA-1 was examined.
(1) Natriuretic peptides may affect the FRET response of NOA-1 because their receptors also possess the cyclase domains to generate cGMP. However, when several cultured cell types including CHO-K1 cells were stimulated with excess concentration of atrial natriuretic peptide, no significant change in the CFP/YFP emission ratio of NOA-1 was observed (FIG. 10A).
(2) When several cultured cell types, including CHO-K1 cells, were stimulated with excess concentration of isoproterenol to generate cAMP, no significant change in the CFP/YFP emission ratio of NOA-1 was observed (FIG. 10B).

These results indicate that the natriuretic peptide stimulation and cAMP generation do not affect the physiologic response of NOA-1 for NO, because the expression of NOA-1 accompanies the overexpression of the NO receptor domain but does not accompany the overexpression of natriuretic peptide receptors. Also, the CGY domain in NOA-1 does not to detect the physiologic concentration of cAMP because of its weak affinity with cAMP.

Example 9

Figure 11:
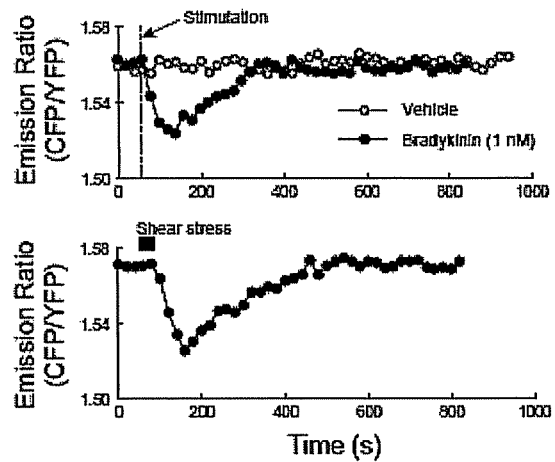
FIG. 11 shows that vascular endothelial cells stably generate the nanomolar range of NO. A, response of NOA-1 for bradykinin and that upon shear stress in vascular endothelial cells; B, pseudocolor images of the CFP/YFP emission ratio in CHO-K 1 and endothelial cells that are expressing NOA-1.
Figure 11:
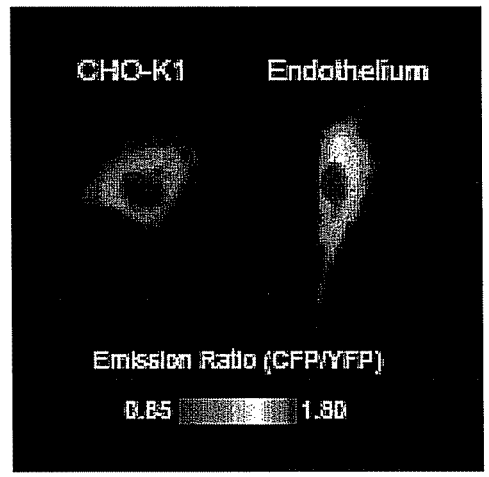

NOA-1 was applied to measure the nanomolar range of NO in vascular endothelial cells.
(1) NOA-1 was expressed in endothelial cells from bovine pulmonary artery cultured in a serum-supplemented media. When the endothelial cells were stimulated with a physiologic concentration of vasoactive hormone, 1 nM bradykinin, a transient change in the CFP/YFP emission ratio was observed (FIG. 11A). We also observed a transient change in the emission ratio by applying shear stress that mimics the blood streaming on the endothelial cells (FIG. 11B). This result confirms that NOA-1 enables the detection of transient generation of NO in vascular endothelial cells upon physiologic stimuli, such as the vasoactive hormone and shear stress.
(2) However, the CFP/YFP emission ratio of NOA-1 was weaker in the vascular endothelial cell than in a nonendothelial CHO-K1 cell (FIG. 11B). This is based on difference of basal NO concentration between CHO-K1 cell and vascular endothelial cell.
(3) Endothelial cells and CHO-K1 cells were pretreated with an inhibitor for nitric oxide synthase (NOS), 1 mM L-NAME and the CFP/YFP emission ratio of NOA-1 was observed.

Figure 12:
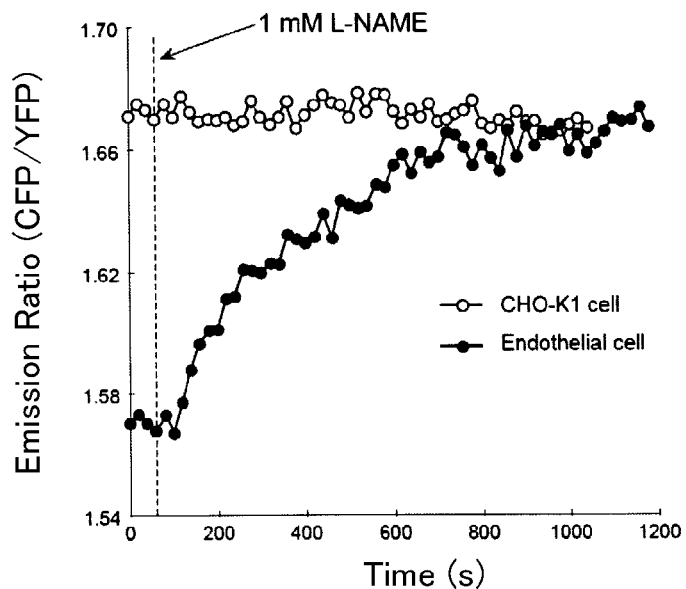
FIG. 12 also shows that vascular endothelial cells stably generate the nanomolar range of NO. A, time course of NOA-1 response in a CHO-K1 cell and an endothelial cell upon L-NAME stimulation; B, changes in the CFP/YFP emission ratio of NOA-1 upon 1 mM L-NAME stimulation in CHO-K1 and endothelial cells.
Figure 12:
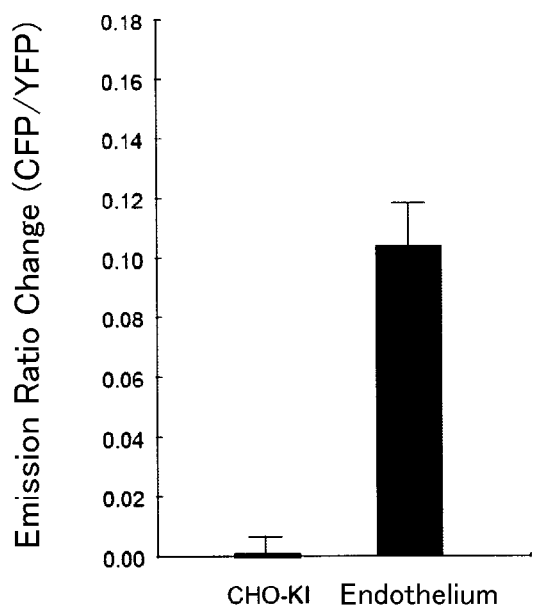

As shown in FIGS. 12A and B, the emission ratio showed no significant change in the nonendothelial CHO-K1 cells probably because of the lack of endogenous endothelial NOS (eNOS). In contrast, the emission ratio gradually increased in the endothelial cells and reached nearly the same level as that in the CHO-K1 cells.
(4) The response of NOA-1 for excess NOC-7 between the endothelial and CHO-K1 cells was compared.

Figure 13:
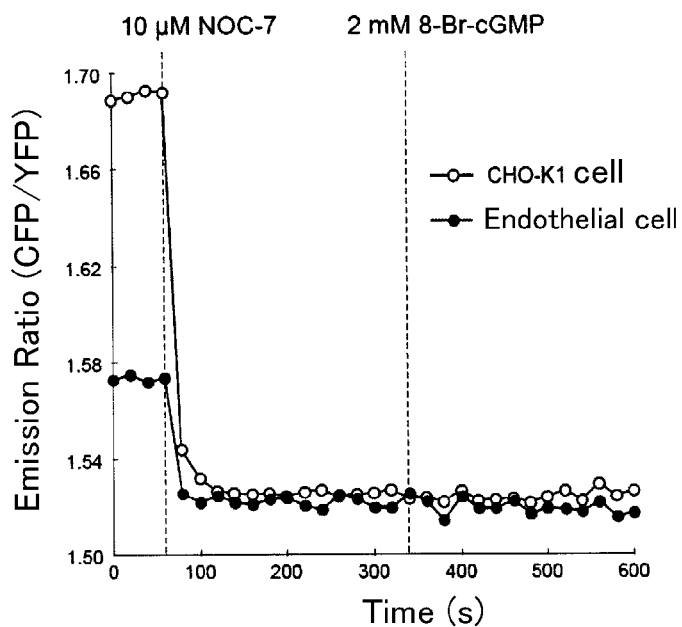
FIG. 13 shows that vascular endothelial cells stably generate the nanomolar range of NO. A, time courses of NOA-1 response in CHO-K1 cell (○) and endothelial cell (●) upon NOC-7 and subsequent 8-Br-cGMP stimulation; B, changes in the CFP/YFP emission ratio of NOA-1 in CHO-K1 (○) and endothelial cells (●) upon NOC-7 stimulation.
Figure 13:
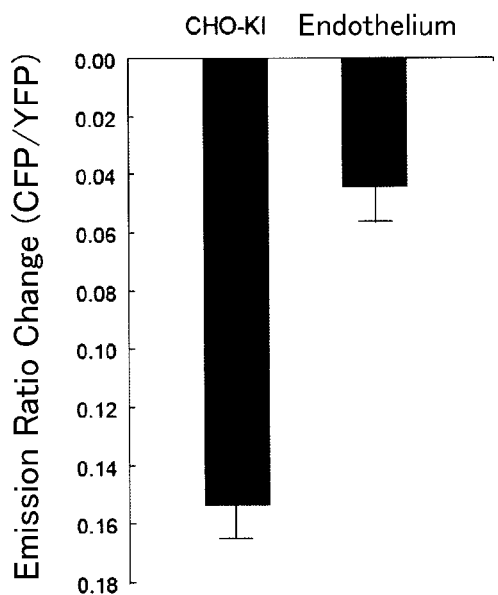

We stimulated the endothelial and CHO-K1 cells with 10 µM NOC-7, which generates enough concentration of NO to immediately saturate the NOA-1 response. Although the basal emission ratios were different between these cells as remarked above, the emission ratios immediately decreased upon stimulation with 10 µM NOC-7 and reached nearly the same plateau level in both of these cells (FIG. 13A). As a result, in endothelial cells, the obtained change in the emission ratio upon the excess NOC-7 stimulation was actually only one-third of that in CHO-K1 cells (FIG. 13B).

Figure 14:
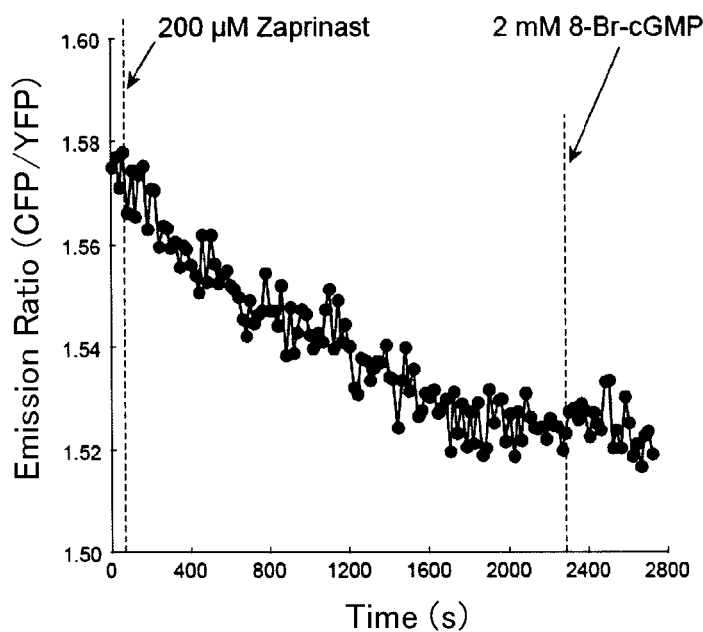
FIG. 14 shows that vascular endothelial cells stably generate the nanomolar range of NO. A, time course of NOA-1 response upon zaprinast and subsequent 8-Br-cGMP stimulation in an endothelial cell; B, changes in the CFP/YFP emission ratio of NOA-1 upon zaprinast stimulation in CHO-K1 and endothelial cells.
Figure 14:
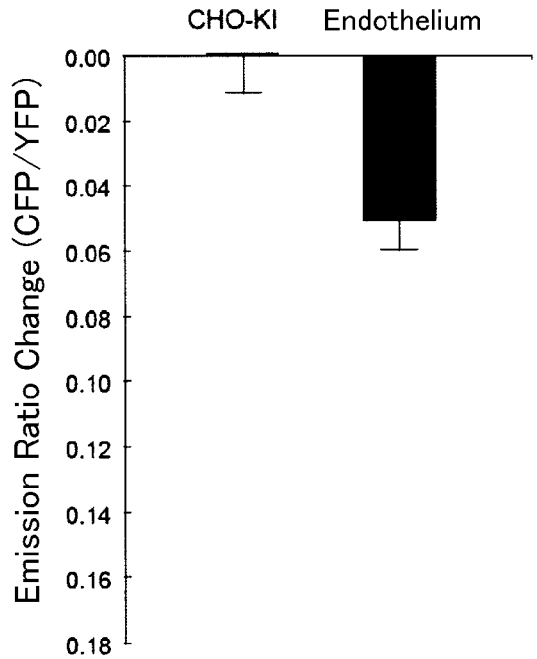
Figure 15:
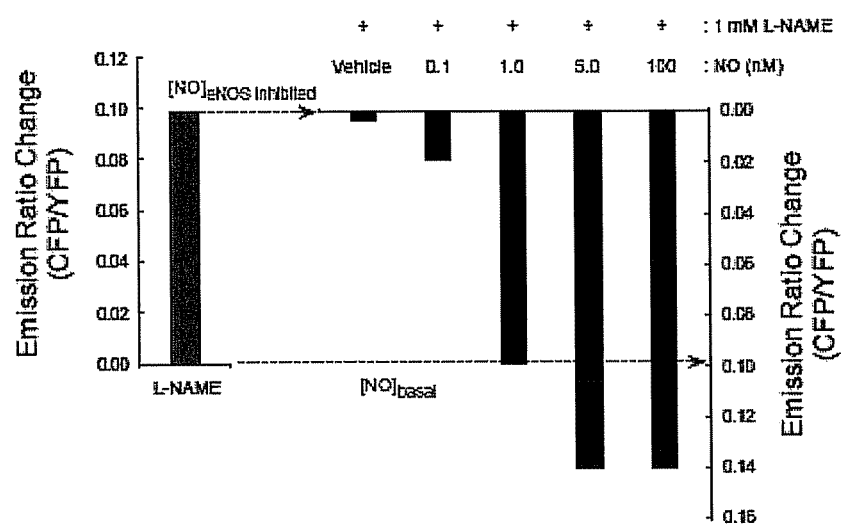
FIG. 15 shows results on basal concentration of NO stably generated in a vascular endothelial cell.

These results demonstrate that the nanomolar range of basal NO is stably generated in vascular endothelial cells. Also, the results indicate that approximately two-thirds of the expressed NOA-1 is involved in the detection of the basal NO in the endothelial cells.
(5) When endothelial cells expressing NOA-1 were treated with 200 µM zaprinast, the CFP/YFP emission ratio gradually decreased and reached the saturation of NOA-1 response (FIG. 14A). In contrast, NOA-1 in CHO-K1 showed no significant change in the emission ratio upon treatment with zaprinast, although the CHO-K1 cells endogenously expressed phosphodiesterases as well (FIG. 14B). This result also supports the generation of basal NO in the endothelial cells.
(6) The basal concentration of NO in each vascular endothelial cell was measured. We first inhibited endogenous eNOS with 1 mM L-NAME to remove the basal NO and cGMP generated by the basal NO. The CFP/YFP emission ratios before and after the inhibition of endogenous eNOS, respectively, represent the basal and zero concentrations of NO in each endothelial cell (FIG. 15). To quantitate the basal concentration of NO, we subsequently added various concentrations of NO to each endothelial cell, in which eNOS activity was inhibited with L-NAME. The peak response of NOA-1 was plotted at each concentration of NO. Based on the obtained dose-response of NOA-1 for various concentrations of NO, we measured 1 nM of the basal NO concentration generated in each endothelial cell.

Example 10

The stable generation of the basal NO concentration was examined in vascular endothelial cells cultured in a serum-containing medium.

(1) The treatment with 2-(4-morpholinyl)-8-phenyl-1(4H)-benzopyran-4-one (LY 294002), a specific inhibitor to phosphatidyl inositol 3-kinase (PI(3)K) removed the basal NO concentration in the endothelial cells. That is, the endothelial cells expressing NOA-1 was added with 100 µM LY 294002), and the CFP/YFP emission ratio was monitored for the NO concentrations in the cells.

Figure 16:
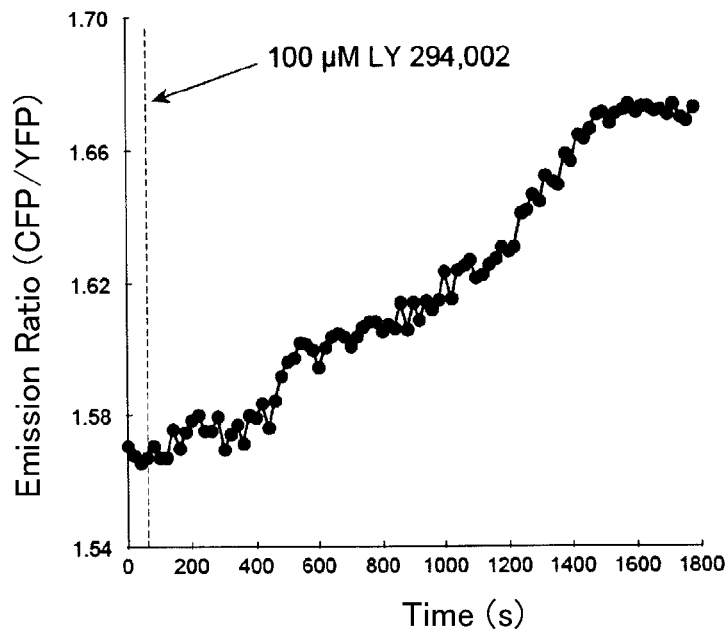
FIG. 16 shows basal NO generation is regulated by PI(3) K-Akt in the vascular endothelial cells. A, time course of NOA-1 response in endothelial cells upon LY 294002 stimulation; B, changes in the CFP/YFP emission ratio of NOA-1 in endothelial cells upon L-NAME and LY 294002 stimulations.
Figure 16:
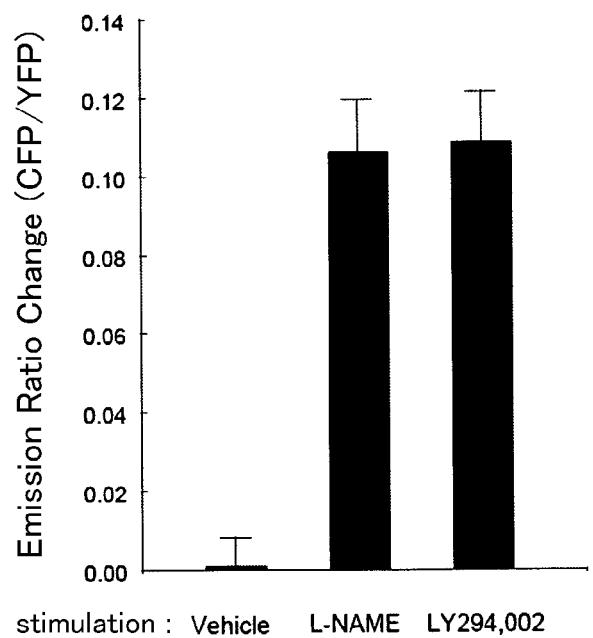

The emission ratio was significantly increased by addition of LY 294002 and reached a plateau within 25 minutes (FIG. 16A). This increase of the emission ratio by LY 294002 was in approximately the same range as in the case of inhibition of eNOS by L-NAME, indicating that LY 294002 has an inhibitory effect on basal NO generation (FIG. 16B).

This result indicates that the PI(3)K activity is deeply involved in stable generation of the basal NO concentration in the vascular endothelial cells.

(2) The signal transduction between the PI(3)K and eNOS activities involved in generation of the basal NO concentration was also examined using protein kinase Akt. A variety of protein kinases including Akt activate eNOS.

In order to examine the action and effect of endogenous Akt in generation of basal NO, a dominant negative mutant of Akt (MAA-Akt; see, for example, Mol. Cell. Biol., 19, 4008-4018, 1999) was expressed in the endothelial cells together with NOA-1. In the MAA-Akt, the 179th lysine is replaced with methionine, the 308th tyrosine and the 473th serine with alanine.

Figure 17:
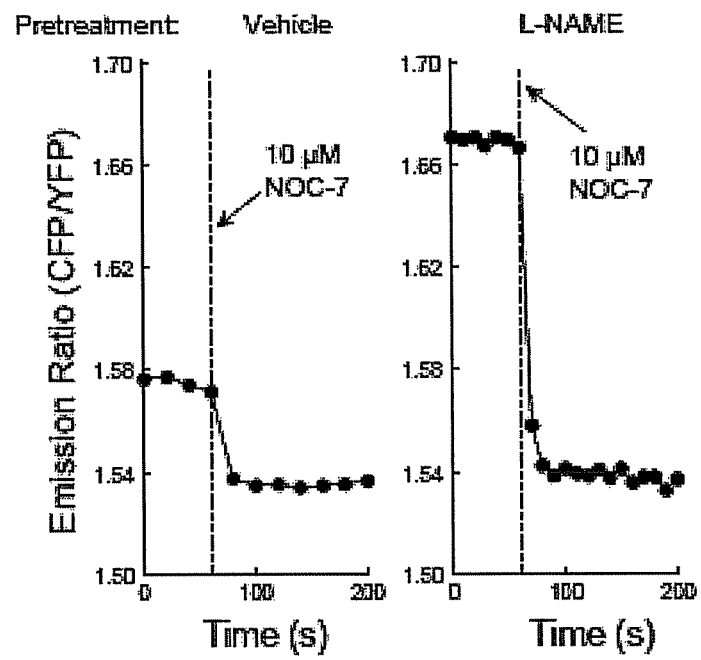
FIG. 17 shows time course of NOA-1 response in endothelial cells upon NOC-7 stimulation. The cells were pretreated with a vehicle solution (control), L-NAME, adenovirus vector expressing MAA-Akt, and adenovirus vector expressing myr-Akt, respectively.
Figure 17:
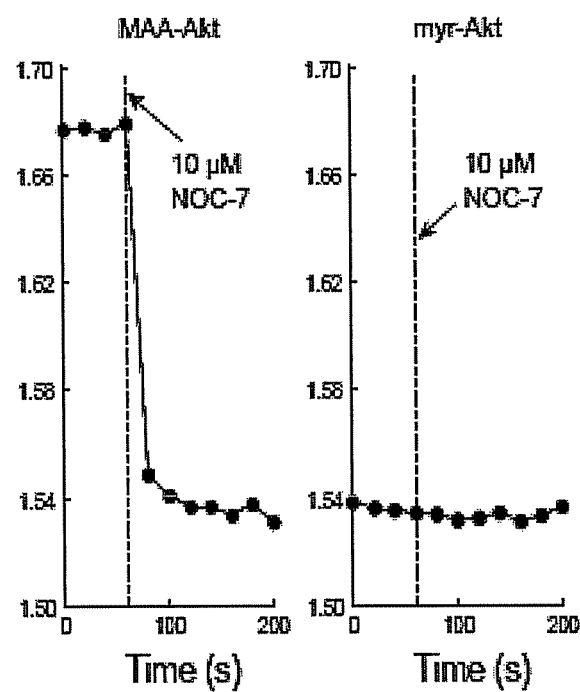

In the endothelial cells expressing MAA-Akt, the emission ratio of NOA-1 was approximately the same as that of pre-treatment with L-NAME, but a significant change could be observed in comparison with the negative control endothelial cells (FIG. 17).

As shown in FIG. 17, when 10 µM NOC-7 was added to the pretreated cell, the CFP/YFP emission ratio immediately reached a plateau level.

Figure 18:
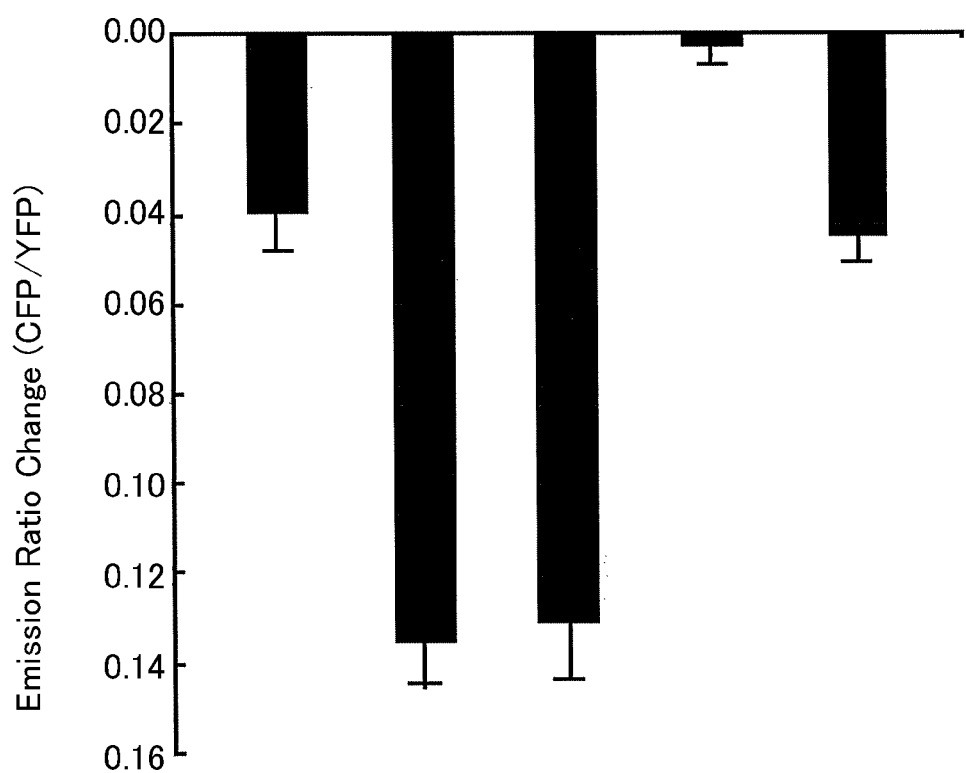
FIG. 18 shows changes in CFP/YFP emission ratio of NAO-1 upon NOC-7 stimulation in endothelial cells. The cells were pretreated with a vehicle solution (control), L-NAME, adenovirus vector expressing MAA-Akt, and adenovirus vector expressing myr-Akt, respectively.

As shown in FIG. 17 and FIG. 18, the change of the emission ratio in the MAA-Akt-expressing cells was 3 times larger than that of the control cells and approximately the same as that of the cells pretreated with L-NAME.

The results indicate that MAA-Akt inhibits generation of basal NO.

(3) As a control for MAA-Akt, a constitutively active mutant (myr-Akt; see, for example, J. Biol. Chem. 278, 28312-28323, 2003) was expressed in the endothelial cells.

As shown in FIG. 18, the emission ratio with myr-Akt was lower than that of the control cells. The response of NOA-1 to 10 µM NOC-7 in the myr-Akt expressing cells was completely lost.

Figure 19:
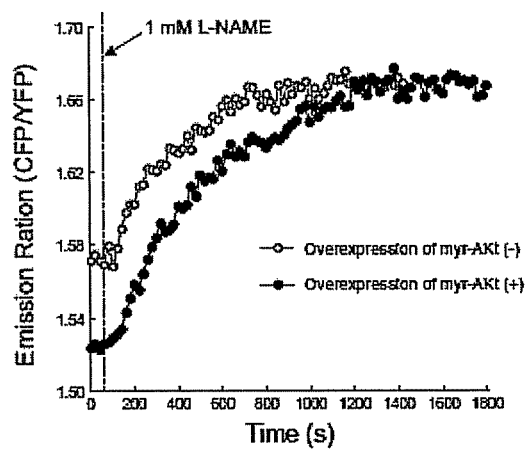
FIG. 19 shows NOA-1 responses in endothelial cells upon various stimulations. A, time course of NOA-1 response in endothelial cells upon L-NAME stimulation with and without myr-Akt (open circle: without myr-Akt; filled circle: with myr-Akt); B, changes in the CFP/YFP emission ratio of NOA-1 in endothelial cells upon L-NAME stimulation with and without myr-Akt; C, time course of NOA-1 response in endothelial cells upon insulin stimulation.
Figure 19:
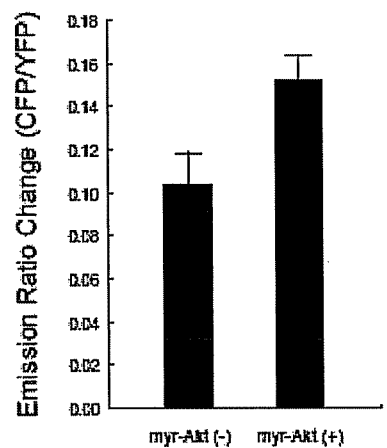
Figure 19:
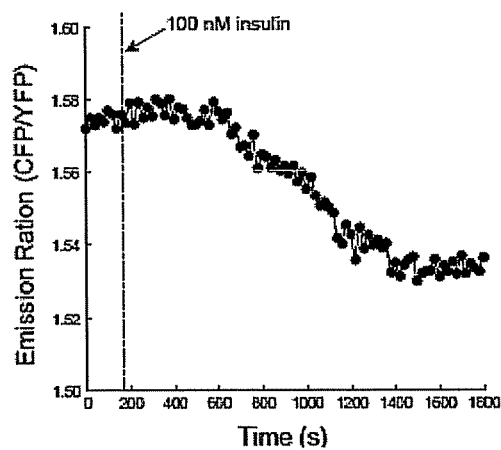

Further, the myr-Akt expressing cells much more increased the CFP/YFP emission ratio in the absence of myr-Akt than that by addition of 1 mM L-NAME (FIGS. 19A and B). This indicates that the Akt activity increases the basal NO concentration.

Considering these results, it is suggested that the Akt activity is induced by the PI(3)K activity to control the eNOS activity for generation of the basal NO concentration in the vascular endothelial cells. In addition, it was also observed that insulin stimulation activates the PI(3)K-Akt pathway and further increases the NO concentration in the endothelial cells (FIG. 19C).

Example 11

Figure 20:
FIG. 20 is schematic representations for cDNA constructs used in Examples. A, the construct for CGY (T178A/T302A); B, the constructs for "sGCα-CGY (T178A/T302A)" in which CGY(T178A/T302A) is connected with α-CGY, and "sGCβ-CGY (T178A/T302A)" (NOA-2) in which CGY(T178A/T302A) is with β-CGY.
Figure 20:
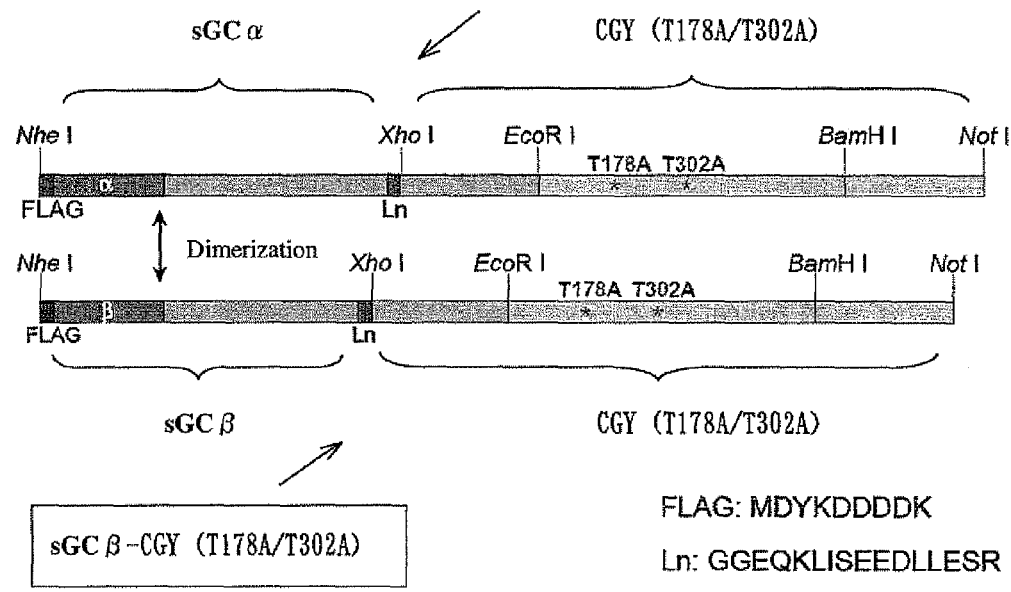

A cDNA (CGY(T178A/T302A)) was prepared so that the 178th and 302nd threonine in the NOA-1 CGY domain was respectively replaced with alanine. The dimer comprising sGCα-CGY(T178A/T302A) and sCGβ-CGY(T178A/T302A) was referred to as "NOA-2" and the emission ratio thereof was compared with NOA-1. FIG. 20 roughly represents block diagrams of CGY(T178A/T302A) and NOA-2. The experiment was carried out basically according to the condition as described in the above Examples.

(1) CHO-K1 cells expressing NOA-1 or NOA-2 were stimulated with various concentrations of NOC-7.

Figure 21:
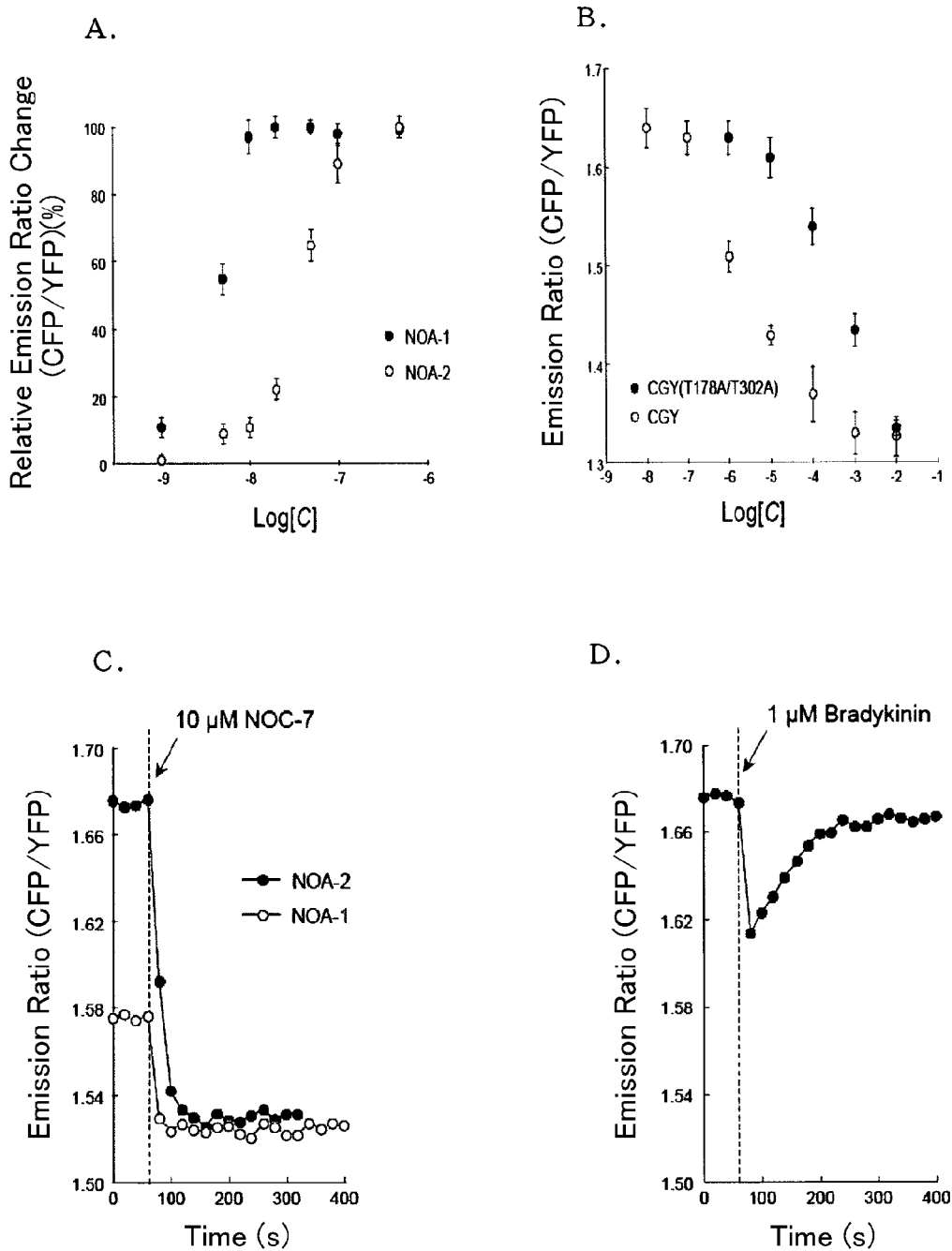
FIG. 21 is comparisons in emission ratio between NOA-1 of FIG. 2 and NOA-2 of FIG. 20. A, dose-responses of NOA-1 and NOA-2 for various concentrations of NOC-7 in CHO-K1 cells; B, dose-responses of CGY and CGY(T178A/T302A) for various concentrations of 8-Br-cGMP in CHO-K1 cells; C, time course of NOA-1 and NOA-2 for NOC-7 stimulation in endothelial cells, and D, time course of NOA-2 for bradykinin stimulation in an endothelial cell.

While the change pattern was slightly different from NOA-1, the CFP/YFP emission ratio was also confirmed in NOA-2 (FIG. 21A).

(2) CHO-K1 cells expressing CGY or CGY(T178A/T302A) were separately stimulated with various concentrations of 8-Br-cGMP. The affinity of CGY(T178A/T302A) to 8-Br-cGMP was 2 order lower than that of CGY (FIG. 21B).

(3) 10 µM NOC-7 was added to endothelial cells, and time course of NOA-1 and NOA-2 were observed. The emission ratio was higher than that of NOA-1 (FIG. 21C).

(4) Endothelial cells were stimulated with 1 µM bradykinin, and time course for response changes of NOA-2 was observed. NOA-2 responded to bradykinin stimulation (FIG. 21D).

(5) From the above results, it was concluded that NOA-2 comprising sCGα-CGY(T178A/T302A) and sCGβ-CGY(T178A/T302A) reacted with NO about 1 order higher than NOA-1.

In addition, when NOA-2 and NOA-1 were separately expressed in endothelial cells, the CFP/YFP emission ratio of NOA-2 was higher than that of NOA-1. This indicates that NOA-2 evades the basal NO in the endothelial cells in comparison with NOA-1. It was also confirmed that the reaction of NOA-2 to 10 µM NOC-7 was greater than NOA-1. Further, NOA-2 also showed a transient response to 1 µM bradykinin in the endothelial cells.

INDUSTRIAL APPLICABILITY

As described above in detail, the invention provides a probe by which a low concentration of NO can be detected and quantified conveniently in high precision.

The invention claimed is:

1. A method for detecting and quantifying nitric oxide in vitro in a cell from an animal cell line or cultured somatic cells, which comprises:

co-expressing in the cell a first hybrid protein consisting of an α-subunit of soluble guanylate cyclase and a first cGMP-visualization probe, and a second hybrid protein consisting of a β-subunit of soluble guanylate cyclase and a second cGMP-visualization probe, and forming a dimer of the first hybrid protein and the second hybrid protein;

contacting the dimer of the first hybrid protein and the second hybrid protein with guanosine 5'-triphosphate in the cell;

detecting a signal from the first cGMP-visualization probe and the second cGMP-visualization probe, wherein the signal indicates the presence of nitric oxide in the cell; and quantifying the amount of nitric oxide in the cell by comparison of the signal change with a calibration curve between nitric oxide concentrations and the signal changes, wherein the first cGMP visualization probe and second cGMP-visualization probe each comprise:

a polypeptide that binds specifically to cyclic guanosine monophosphate (cGMP), wherein the polypeptide is cGMP-dependent protein kinase Iα in which amino acids 1-47 are deleted, and two chromophores, cyan fluorescent protein and yellow fluorescent protein, one of which is linked to the N-terminal of the polypeptide and the other of which is linked to the C-terminal of the polypeptide, and wherein the method is capable of detecting a 1 nanomolar concentration of nitric oxide in the cell.

* * * * *

SEQUENCE LISTING

<160> NUMBER OF SEQ ID NOS: 2

<210> SEQ ID NO 1
<211> LENGTH: 16
<212> TYPE: PRT
<213> ORGANISM: Artificial
<220> FEATURE:
<223> OTHER INFORMATION: Synthetic Construct

<400> SEQUENCE: 1

Gly Gly Glu Gln Lys Leu Ile Ser Glu Glu Asp Leu Leu Glu Ser Arg
1               5                   10                  15

<210> SEQ ID NO 2
<211> LENGTH: 9
<212> TYPE: PRT
<213> ORGANISM: Artificial
<220> FEATURE:
<223> OTHER INFORMATION: Synthetic Construct

<400> SEQUENCE: 2

Met Asp Tyr Lys Asp Asp Asp Asp Lys
1               5